United States Patent [19]

Brown

[11] Patent Number: 4,910,819
[45] Date of Patent: Mar. 27, 1990

[54] CT-SCANNER PROTECTIVE COVER AND METHOD THEREFORE

[76] Inventor: Timothy E. Brown, 107 E. McKinley, Tempe, Ariz. 85281

[21] Appl. No.: 334,468

[22] Filed: Apr. 7, 1989

[51] Int. Cl.⁴ .............................................. A47G 9/04
[52] U.S. Cl. .......................................... 5/484; 5/482; 5/496; 378/209
[58] Field of Search .................... 5/482, 484, 495–499; 378/209; 269/327, 322; 108/90

[56] References Cited

U.S. PATENT DOCUMENTS

| | | | |
|---|---|---|---|
| 2,641,001 | 6/1953 | Frasnov | 5/499 |
| 3,956,782 | 5/1976 | Morrison | 5/484 |
| 4,244,066 | 1/1981 | Rukawina | 5/484 |
| 4,274,169 | 6/1981 | Standlford | 5/502 |
| 4,627,363 | 12/1986 | Jones | 108/90 |

Primary Examiner—Alexander Grosz
Attorney, Agent, or Firm—Harry M. Weiss

[57] ABSTRACT

A CT-scanner includes a patient cushion that fits over a baseplate. Both the cushion and the baseplate have complementary lengthwise fastener strips. A cover of the scanner includes a vinyl central sheet that drapes over side rails of the scanner to form overhang flaps. Each of the flaps is sewn onto a sheeted section that has longitudinal velcro strips. When the sheeted sections are tucked between the baseplate and the cushion, the fastener strips of the sheeted section fasten to the velcro strips of the cushion and the baseplate. A head end of the central sheet is contoured to fit over a head rest of the scanner and cause a funneling of fluids onto the center of the central sheet from the head of a patient in either a supine or prone position on the cover.

12 Claims, 1 Drawing Sheet

CT-SCANNER PROTECTIVE COVER AND METHOD THEREFORE

BACKGROUND OF THE INVENTION

1. Field of Invention

This invention generally relates to medical radiologic equipment and methods therefore and, more particularly, to a protective cover for a cushion that rests on a baseplate of a CT-scanner and method therefore.

2. Background of the Invention

A heavily utilized piece of hospital equipment, known as a CT-(computer aided tomography) scanner, is used in a plethora of diagnostic procedures. The procedures are for medical cases ranging from simple outpatient cases to level-one trauma cases.

The scanner includes a baseplate about seven feet long. In a typical diagnostic procedure, a patient is placed either in a supine or a prone position on a patient cushion that rests upon the baseplate. Usually, the cushion and the baseplate have complimentary lengthwise fastener strips, such as the ones sold under the trademark of VELCRO strips that maintain the cushion in a fixed position on the baseplate. The cushion and the baseplate form what is known as a cradle.

The cradle rests upon what is known as an intermediate structure the houses much of the scanner's electro mechanical control components. The intermediate structure is sandwiched between a pair of table side rails that are substantially as long as the cradle.

The cradle may be driven longitudinally by a motor in the intermediate structure. Additionally, the intermediate structure may be driven longitudinally by a motor in the table base, thereby providing a telescoping of the cradle and the intermediate structure.

Frequently, body fluids, such as blood and urine, flow from the patient, between the side rails and the cradle, onto the intermediate structure. When the procedure utilizes a radiologic contrast solution, it also may flow onto the intermediate structure.

Often, the fluids and the contrast solution penetrate to the interior of the intermediate and flow onto the electro mechanical components. A result of the flow of the fluids and the contrast solution is a need to clean the scanner. The scanner cannot be used for the diagnostic procedures while it is being cleaned. Accordingly, the flow of the fluids and the contrast solution reduces utilization of the scanner.

It should be appreciated that because of the construction of the scanner, it is impractical to thoroughly clean the scanner as a matter of routine. What usually remains after the cleaning is an unsanitary residue. Moreover, there is a cumulative increase in the residue over the life of the scanner. Therefore, the scanner is frequently used under cumulatively unsanitary conditions.

Heretofore, there has not been a cover that prevents the fluids and the contrast solution from flowing onto the electro mechanical control components of the scanner.

SUMMARY OF THE INVENTION

An object of the present invention is to prevent a flow of fluids and contrast solution onto electro mechanical control components of a CT-scanner and method therefore.

Another object of the present invention is to provide a cover of a patient cushion of a CT-scanner that prevents a flow of fluids and contrast solution onto electro mechanical control components of a CT-scanner and method therefore.

According to the present invention a central sheet is adapted to cover a patient cushion that rests on a baseplate of a CT-scanner, with the width of the central sheet being great enough to form flaps that drape over side rails of the scanner. A sheeted section, connected to the central sheet, has lengthwise cloth fastener strips on opposite sides thereof. The sheeted section may be tucked between the cushion and the baseplate where one of the cloth fastener strips of the sheeted section connects to a cloth fastener strip on the cushion and the other cloth fastener strip of the sheeted section connects to a cloth fastener strip on the baseplate.

A protective cover of the present invention is preferably made from 20 mil flexible vinyl sheets. The cover preferably includes a contoured head end adapted to cover a head rest of the scanner. The contoured end causes fluids from the head of a patent to be funneled onto a central sheet of the cover.

These and other objects, features and advantages of the present invention, as well as details of the preferred embodiment thereof, will be more fully understood from the following description and drawing.

DESCRIPTION OF THE PREFERRED EMBODIMENT

Figure 1:
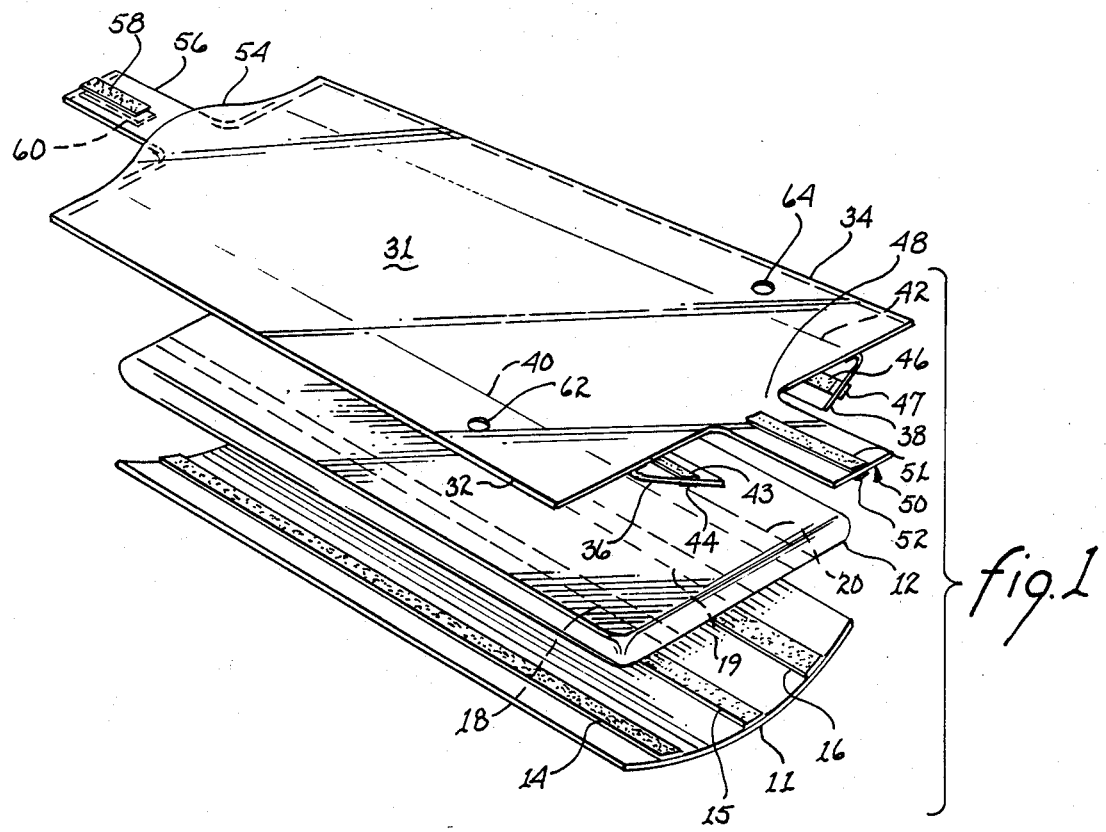
FIG. 1 is a perspective view of the preferred embodiment of the present invention.
Figure 2:
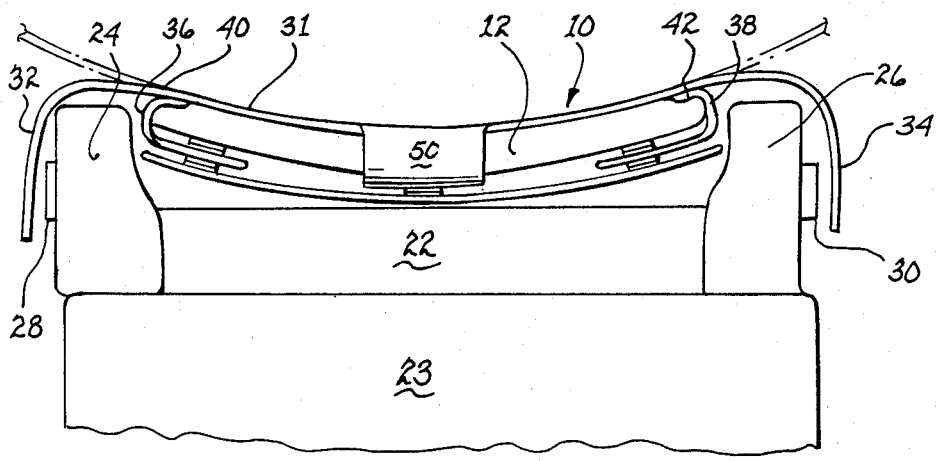
FIG. 2 is an end view of the preferred embodiment of the present invention.

Referring to FIGS. 1 and 2, a cradle 10 (FIG. 2) of a CT-scanner is comprised of a baseplate 11 and a patient cushion 12. Moreover, cushion 12 is adapted to rest upon baseplate 11. It should be understood that cushion 12 is of a size suitable for an adult to rest thereon in either a supine or a prone position. As explained hereinafter, cradle 10 additionally includes a protective cover.

In accordance with the prior art, baseplate 11 includes lengthwise fastener strips 14, 15, 16 (FIG. 1) that are parallel to each other. Strip 15 is along the center of baseplate 11. Strips 14, 16 are symmetrically disposed on opposite sides of strip 15.

Cushion 12 includes lengthwise fastener strips 18, 19, 20 on its underside 21 (FIG. 2) that are complementary to strips 14, 15, 16 (FIG. 1), respectively. Accordingly, when cushion 12 is placed on baseplate 11, strips 14, 18, strips 15, 19 and strips 16, 20 are fastened together.

Cradle 10 is moveably coupled to an intermediate structure 22 that houses much of the scanner's electro mechanical components. Intermediate structure 22 includes a motor and transmission linkages that are operable to move cradle 10 longitudinally. Additionally, intermediate structure 22 is moveably coupled to a table base 23 that includes a motor and transmission linkages that are operable to move intermediate structure 22 longitudinally, thereby providing a telescoping of cradle 10 and intermediate structure 22.

Cradle 10 and intermediate structure 22 are sandwiched between table side rails 24, 26 that are fixedly connected to intermediate structure 22. Side rails 24, 26 are substantially as long as cradle 10. Similar control panels 28, 30 are carried by side rails 24, 26 respectively.

In this embodiment, the protective cover includes a vinyl central sheet 31 that has a length substantially equal to the length of cradle 10. Sheet 31 has a width that causes it to drape over side rails 24, 26 and form flaps 32, 34 that extend below panels 28, 30, respectively. Because of flaps 32, 34 body fluids, such as blood and urine, and contrast solution cannot flow onto panels 28, 30. Additionally, sheet 31 prevents the body fluids and the contrast solution from flowing over cradle 10 onto intermediate structure 22.

The protective cover additionally includes sheeted sections 36, 38 that are sewn to sheet 31 near a proximal end 40 of flap 32 and near a proximal end 42 of flap 34, respectively. Sections 36, 38 are approximately the same size as flaps 32, 34. Preferably, sections 36, 38 are sewn to sheet 31 with nylon thread.

Section 36 has on opposite sides thereof lengthwise fastener strips 43, 44 that are sewn on with nylon thread. When section 36 is tucked between cushion 12 and baseplate 11, strips 18, 43 and strips 14, 44 are connected together.

Section 38 has on opposite sides thereof lengthwise fastener strips 46, 47, similar to strips 43, 44, respectively, that are sewn on with nylon thread. When section 38 is tucked between cushion 12 and baseplate 11, strips 20, 46 and strips 16, 47 are connected together. When sections 36, 38 are both tucked between cushion 12 and baseplate 11, sheet 31 is securely maintained upon cushion 12.

Preferably, sheet 31 has a foot 48 with a central portion that is integral with a tongue, 50. Tongue 50 has on opposite sides thereof centrally disposed lengthwise fastener strips 51, 52. When tongue 50 is tucked between cushion 12 and baseplate 11, strips 15, 51 and strips 19, 52 are connected together.

Sheet 31 additionally has a contoured head end 54 that is adapted to fit over a head rest (not shown). The head rest has an end that fits between the protective cover and baseplate 11. End 54 creates a funnel that causes fluid from the head of the patient to be funneled towards the center of sheet 31.

A central part of sheet 31, near end 54, is sewn to a tongue 56 similar to tongue 50 described hereinbefore. It should be understood that tongue 56 is extendable below end 54 (FIG. 1). Tongue 56 has on opposite sides thereof centrally disposed velcro strips 58, 60. When tongue 56 is tucked between cushion 12 and baseplate 11, strips 15, 58 and strips 19, 60 are connected together.

Preferably, flaps 32, 34 include grommeted holes 62, 64, respectively, where catheter bags may be suspended.

While the invention has been particularly shown and described with reference to a preferred embodiment thereof, it will be understood by those skilled in the art that changes in form and detail may be made therein without departing from the spirit and the scope of the invention.

I claim:

1. A protective covering of a CT-Scanner of the type that has a patient cushion adapted for connection to a baseplate via complementary lengthwise cloth fastener strips on said cushion and on said baseplate, said baseplate and said cushion being sandwiched between side rails of said scanner, comprising:
a substantially fluid impervious central sheet that has a length substantially equal to the length of said cushion and a width that causes a formation of flaps that drape over said side rails when said central sheet is placed upon said cushion;
a sheeted section, approximately the size of a flap, connected to one of said flaps; and
means for connecting said sheeted section between said cushion and said baseplate.

2. The protective covering of claim 1 wherein said means comprises a pair of complementary cloth fastener strips, connected to opposite sides of said sheeted section, that are adapted for connection to said cloth fastener strips of said cushion and said baseplate when said sheeted section is tucked therebetween.

3. The protective covering of claim 2 wherein said fastener strips are VELCRO.

4. The protective covering of claim 3 wherein nylon thread is used for connecting said sheeted section to said flap and for connecting velcro strips to said central sheet and to said cushion.

5. The protective covering of claim 1 additionally comprising a tongue that is connected to the foot of said central sheet; and
a pair of complementary cloth fastener strips, connected to opposite sides of said tongue, that are adapted for connection to said cloth fastener strips of said cushion and said baseplate when said tongue is tucked therebetween.

6. The protective covering of claim 5 wherein said fastener strips are VELCRO.

7. The protective covering of claim 1 wherein said central sheet has a contoured head end adapted to fit over a head rest of said scanner, said contoured head end forming a funnel for fluids from the head of a patient in either a supine or a prone position upon said covering.

8. The protective covering of claim 7, additionally comprising:
a tongue connected to a portion of said central sheet near said head end; and
a pair of complementary cloth fastener strips, connected to opposite sides of said tongue, that are adapted for connection to said cloth fastener strips of said cushion and said baseplate when said tongue is tucked therebetween.

9. The protective covering of claim 1 wherein said flap has a grommeted hole therethrough.

10. The protective covering of claim 1 wherein said sheets are made from vinyl.

11. In the method of preventing body fluids and contrast solution from flowing onto mechanical and electronic elements of a CT-scanner of the type the has a patient cushion that rests on a baseplate, the steps of:
covering said cushion with a vinyl central sheet that drapes over side rails of said scanner to form flaps; and
fastening a vinyl sheeted section to said cushion and said baseplate, said sheeted section being connected to one of said flaps.

12. The method of claim 11 including the additional step of covering a head rest of said scanner with a contoured head end of said central sheet to cause fluid from a head of a patient resting thereon to be funneled onto a central portion of said central sheet.

* * * * *